United States Patent [19]

Yamaguchi et al.

[11] 4,294,921
[45] Oct. 13, 1981

[54] METHOD OF HARDENING GELATIN

[75] Inventors: Jun Yamaguchi; Takashi Naoi; Hidefumi Sera; Kunio Ishigaki; Masasi Ogawa, all of Minami-ashigara, Japan

[73] Assignee: Fuji Photo Film Co., Ltd., Minami-ashigara, Japan

[21] Appl. No.: 162,235

[22] Filed: Jun. 23, 1980

[30] Foreign Application Priority Data

Jun. 22, 1979 [JP] Japan .................. 54-78686

[51] Int. Cl.³ .............. G03C 1/30; C08L 89/00; B01J 13/02
[52] U.S. Cl. ........................ 430/621; 430/622; 430/623; 430/626; 260/8; 260/117; 264/4; 252/316; 106/125
[58] Field of Search ............. 260/8, 117; 430/621, 430/622, 623, 624, 625, 626, 628, 138; 264/4; 252/316; 106/125

[56] References Cited

U.S. PATENT DOCUMENTS 3,926,869 12/1975 Horie et al. ................ 260/8

Primary Examiner—Won H. Louie, Jr.
Attorney, Agent, or Firm—Sughrue, Mion, Zinn, Macpeak & Seas

[57] ABSTRACT

A method of hardening gelatin which uses both a gelatin hardener and a polymer having a repeating unit of the formula (I):

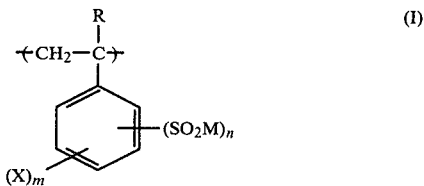

wherein R represents a hydrogen atom, an alkyl group having 1 to 6 carbon atoms, and a halogen atom; M represents a hydrogen atom, an alkali metal atom, an alkali earth metal atom, or an organic base; X represents an alkyl group having 1 to 6 carbon atoms, an alkoxy group, an alkylamino group, or a halogen atom; m represents 0, 1 or 2; and n represents 1 or 2.

9 Claims, No Drawings

METHOD OF HARDENING GELATIN

BACKGROUND OF THE INVENTION

1. Field of the Invention

This invention relates to an improved method for hardening gelatin, and more particularly, to a method for quickly hardening gelatin used in a silver halide photosensitive material. The following description assumes photosensitive materials as typical examples of the application of gelatin.

2. Description of the Prior Art

Gelatin is used as a binder for various photographic light-sensitive materials such as a silver halide emulsion layer, an emulsion protective layer, a filter layer, an interlayer, an anti-halation layer, a backing layer, a film base subbing layer and a baryta layer, and all these layers contain gelatin as a primary component.

These gelatin-containing photosensitive materials are treated with various aqueous solutions having different pHs or temperatures. Those layers which contain gelatin yet to be treated with a hardener depend primarily upon the physical properties of gelatin and are low in water resistance. In aqueous solution, they swell excessively and become very weak in mechanical strength, and in extreme cases, the gelatin layer may dissolve out in an aqueous solution having a temperature higher than 30° C. or in a strong alkaline aqueous solution. These defects are fatal to the use of the gelatin layer as a constituent of a photographic light-sensitive material.

Many compounds have been known to be effective in hardening gelatin to provide a gelatin layer having high resistance to water, heat and physical injury. These compounds are so called "gelatin hardeners" and conventionally used in the production of photographic light-sensitive materials. Illustrative gelatin hardeners include aldehyde compounds such as formaldehyde and glutaraldehyde; compounds having reactive halogen as described in U.S. Pat. No. 3,635,718; compounds having a reactive ethylenically unsaturated bond as described in U.S. Pat. No. 3,635,718; aziridine compounds as described in U.S. Pat. No. 3,017,280; epoxy compounds as described in U.S. Pat. No. 3,091,537; halogenocarboxyaldehydes such as mucochromic acid; dioxanes such as dihydroxydioxane and dichlorodioxane; vinyl sulfones as described in U.S. Pat. Nos. 3,642,486 and 3,687,707; vinyl sulfone precursors as described in U.S. Pat. No. 3,841,872; keto-vinyls as described in U.S. Pat. No. 3,640,720; or inorganic hardeners such as chrome alum and zirconium sulfate.

However, these known gelatin hardeners are defective in one way or another: some of them do not exhibit adequate hardening effect when used in a photographic light-sensitive material; others require a long time for hardening gelatin; still others are made of compounds difficult to synthesize and cannot be synthesized in great quantities; other hardeners are unstable and do not keep long; some smell so bad that their production efficiency is very low; still others are harmful to the human body.

Hardeners providing a particularly high hardening rate are required to have high reactivity and unavoidably they have several defects; for one thing, due to their high reactivity, they are unstable and have a tendency to decompose during their synthesis and for this reason, they are difficult to synthesize in great quantities. For another, highly reactive hardeners easily react with moisture in air and do not keep long. They also decompose rapidly in an aqueous solution or aqueous dispersion in which they are used, and this reduces the amount of the hardener effective for the reaction of hardening and the desired degree of hardening may not be obtained. In addition, such hardeners, their starting materials, and intermediates seem to have harmful effects on the human body, such as carcinogenicity and skin-irritating effect.

But on the other hand, the technology for achieving rapid hardening of the gelatin-containing layer of a photographic light-sensitive material is important to the photographic industry. It is known that the degree to which the gelatin-containing layer is hardened often presents a critical effect on the photographic characteristics of that layer. Therefore, in the photographic industry, light-sensitive materials can be sold to the consumer only after they went through the hardening reaction to provide stable photographic characteristics. This means the manufacturer of photosensitive materials must keep their product in stock until it is completely hardened. The cost of storage is very high, and the longer the time required for hardening, the greater the storage cost. Some manufacturers have tried to increase the hardening rate of photosensitive materials on storage by some means such as heating or humidifying. But such treatment has not been altogether satisfactory because it adversely affects the photographic characteristics of the photosensitive material on storage, or blocking occurs in the roll of photosensitive material. Thus, although an effective method for rapidly hardening gelatin has long been desired in the industry it has been difficult to meet this demand by modifying a gelatin hardener per se.

SUMMARY OF THE INVENTION

One object of this invention is to provide a method for hardening gelatin at a fast rate.

Another object is to provide a method for hardening gelatin at a fast rate using a compound which is stable and easy to synthesize.

A further object is to provide a method for hardening gelatin at a fast rate in which adequate provisions are made against pollution and explosion of an organic solvent in which a hardener is dissolved for addition to the photosensitive material as well as against the adverse effect of the hardener on the human body.

Still another object is to provide a silver halide photographic light-sensitive material in which gelatin is hardened at a fast rate.

Yet another object is to provide a method for hardening gelatin at a fast rate without adversely affecting the characteristics of a silver halide photographic light-sensitive material.

These objects of this invention can be achieved by a gelatin hardening method that uses both a gelatin hardener and a polymer having a repeating unit of the following formula (I):

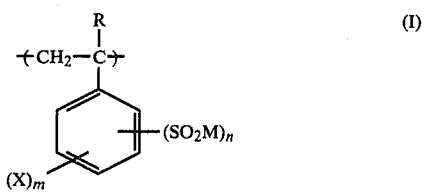

wherein R represents a hydrogen atom, an alkyl group having 1 to 6 carbon atoms such as methyl or ethyl, and a halogen atom such as chlorine or bromine; M represents a hydrogen atom, an alkali metal atom such as sodium or potassium, an alkali earth metal atom such as calcium or magnesium, or an organic base such as trimethylamine or triethylamine; X represents an alkyl group having 1 to 6 carbon atoms, an alkoxy group, an alkylamino group, or a halogen atom; m represents 0, 1 or 2; and n represents 1 or 2.

DETAILED DESCRIPTION OF THE INVENTION

The polymer having a repeating unit of the formula (I) above includes a homopolymer produced by polymerizing a monomer of the formula (II) below, a copolymer produced by polymerizing a monomer of the formula (II) with a monomer having at least one other addition-polymerizable unsaturated bond, and a polymer produced by introducing a sulfinic group at side chains of the above mentioned polymers, as well as derivatives of these polymers:

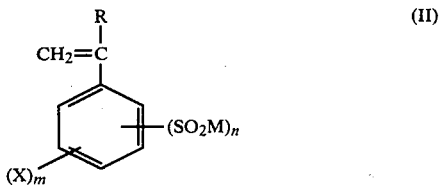

wherein R represents a hydrogen atom, an alkyl group having 1 to 6 carbon atoms such as a methyl group or ethyl group, or a halogen atom such as chlorine or bromine; M represents a hydrogen atom, an alkali metal atom such as sodium or potassium, an alkali earth metal atom such as calcium or magnesium, or an organic base such as trimethylamine or triethylamine; X represents an alkyl group having 1 to 6 carbon atoms, alkoxy, alkylamino or a halogen atom; m represents 0, 1 or 2; and n represents 1 or 2.

In the formulae (I) and (II) described above, M preferably represents an alkali metal, particularly preferably sodium or potassium; X preferably represents a lower alkyl group, particularly preferably a methyl group; m preferably represents 0; and n preferably represents 1.

Illustrative monomers of the formula (II) include:

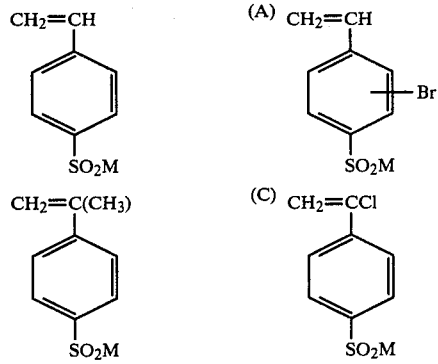

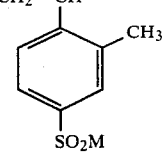

and a particularly preferred monomer is a compound of (A). The monomer (A) can be synthesized by the method described in *Chemistry Letters*, pp. 419–420 (1976), and the synthesis of the monomer is not limited to that particular method. The other monomers can be synthesized by that method or by reduction with a reducing agent such as sodium sulfite followed by optional vinyl formation, provided that the corresponding sulfonic acid chloride is prepared first.

A polymer such as polystyrene may be used as a starting material for polymer reaction that is carried out in the same method for introducing a sulfinic group to the monomer to produce a polymer having a repeating unit of the formula (I).

Any monomer that has at least one addition-polymerizable unsaturated bond can be used as the monomer copolymerizable with the monomer of the formula (II). Such addition-polymerizable unsaturated compounds include allyl compounds such as allyl esters (e.g. allyl acetate, allyl caproate, allyl caprylate, allyl laurate, allyl palmitate, allyl stearate, allyl benzoate, allyl acetoacetate and allyl lactate), allylethoxyethanol, allyl butyl ether, allyl glycidyl ether and allyl phenyl ether; vinyl ethers (e.g. methyl vinyl ether, butyl vinyl ether, hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether, tetrahydrofurfuryl vinyl ether, vinyl phenyl ether, vinyl tolyl ether, vinyl chlorophenyl ether, vinyl-2,4-dichlorophenyl ether, vinyl naphthyl ether and vinyl anthranyl ether; vinyl esters such as vinyl acetate, vinyl propionate, vinyl butyrate, vinyl isobutyrate, vinyl dimethyl propionate, vinyl ethyl butyrate, vinyl valerate, vinyl caproate, vinyl chloroacetate, vinyl dichloroacetate, vinyl methoxyacetate, vinyl butoxyacetate, vinyl phenyl acetate, vinyl acetoacetate, vinyl lactate, vinyl-β-phenylbutyrate, vinylcyclohexylcarboxylate, vinyl benzoate, vinyl salicylate, vinyl chlorobenzoate, vinyl tetrachlorobenzoate and vinyl naphthoate; vinyl heterocyclic compounds such as N-vinyl oxazolidone, N-vinylimidazole, N-vinylpyrrolidone, N-vinylcarbazole, vinyl thiophene and N-vinylethyl acetamide; styrenes (e.g. styrene, methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, acetoxymethylstyrene, methoxystyrene, 4-methoxy-3-methylstyrene, dimethoxstyrene, chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene, 4-fluoro-3-trifluoromethylstyrene and methyl vinylbenzoate ester); crotonic acids such as crotonic acid, crotonic acid amide, crotonate ester (e.g. butyl crotonate, hexyl crotonate and glycerin monocrotonate); vinyl ketones (e.g. methyl vinyl ketone, phenyl vinyl ketone and methoxyethyl vinyl ketone); olefins (e.g. dicyclopentadiene, ethylene, propylene, 1-butene, 1-pentene, 1-hexene, 4-methyl-1-pentene, 1-heptene, 1-octene, 1-decene, 5-methyl-1-nonene, 5,5-dimethyl-1-octene, 4-methyl-1-hexene, 4,4-dimethyl-1-pentene, 5-methyl-1-hexene, 4-methyl-1-heptene, 5-methyl-1-heptene, 4,4-dimethyl-1-hexene, 5,6,6-trimethyl-1-heptene, 1-dodecene and 1-octadecene); itaconic acids (e.g. itaconic acid, itaconic anhydride, methyl itaconate and ethyl itaconate); sorbic acid, cinnamic acid, methyl sorbate, glycidyl sorbate, citraconic acid, chloroacrylic acid, mesaconic acid, maleic acid, furmaric acid, halogenated olefins (e.g. vinyl chloride, vinylidene chloride and isoprene), unsaturated nitriles (e.g. acrylonitrile and methacrylonitrile), acrylic acids such as acrylic acid, methyl acrylate, methacrylic acids such as methacrylic acid and methyl methacrylate, acrylamides and methacrylamides.

Of these addition-polymerizable unsaturated compounds, styrenes, vinyl heterocyclic compounds, vinyl ethers, vinyl esters and olefins are particularly preferred.

The polymer that can be used in this invention must contain at least 0.01 mol%, preferably at least 0.1 mol%, more preferably at least 1 mol%, of the repeating unit of the formula (I). If the polymer contains less than 0.01 mol% of the repeating unit of the formula (I), it is by no means capable of accelerating the hardening speed of gelatin. The intended objects of this invention can be obtained by using at least one of the above polymers in an amount of from about 0.01 to 99 wt%, preferably from about 0.1 to 50 wt%, more preferably from about 1 to 20 wt%, depending on the polymer and gelatin used, based on the sum of the solid content of gelatin and the polymer. The polymer used in too small an amount is not very effective, and using an excessive amount of the polymer gives too viscous a coating solution, and this may result in difficult application of the solution or gelatin which does not set. The polymers defined above preferably have a number average molecular weight of from about 1,000 to 2,000,000, more preferably from about 10,000 to 500,000. The polymer having too low a molecular weight is not very effective, and using a polymer having an excessively high molecular weight may give a too viscous coating solution.

Illustrative polymers that can be used in this invention are set forth below, wherein the proportion of constituent monomers is indicated in terms of the molar ratio.

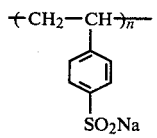
(1)

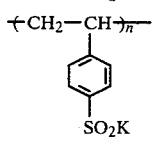
(2)

-continued

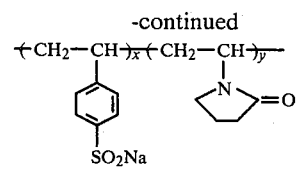
(3)

x/y = 80/20

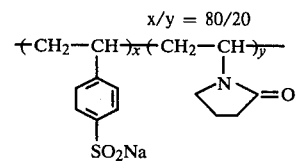
(4)

x/y = 50/50

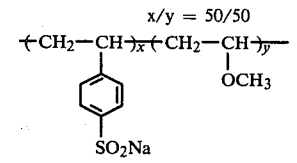
(5)

x/y = 50/50

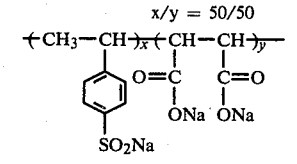
(6)

x/y = 50/50

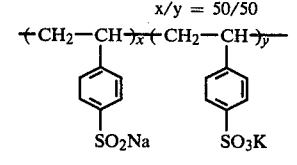
(7)

x/y = 75/25

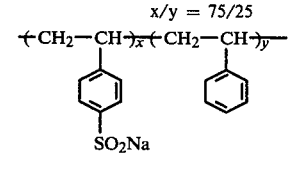
(8)

x/y = 70/30

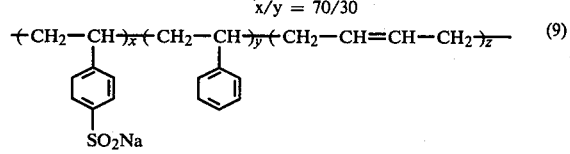
(9)

x/y/z = 50/20/30

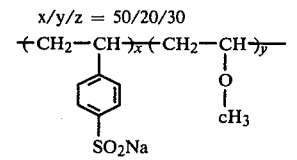
(10)

x/y = 60/40

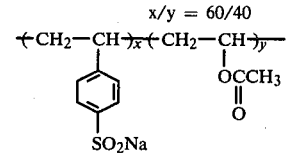
(11)

x/y = 80/20

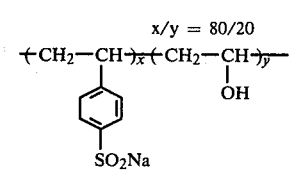
(12)

x/y = 80/20

-continued

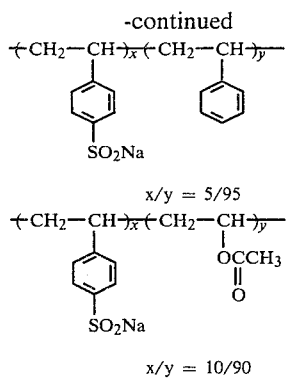

$x/y = 5/95$ $x/y = 10/90$

Examples of the gelatin hardener that can be used in this invention include aldehydes (e.g. formaldehyde, glyoxal and glutaraldehyde), N-methylol compounds (e.g. dimethylolurea and methyloldimethylhydantoin), dioxane derivatives (e.g. 2,3-dihydroxydioxane), active vinyl compounds (1,3,5-triacryloylhexahydro-s-triazine and bis(vinylsulfonyl)methyl ether), active halogen compounds (e.g. 2,4-dichloro-6-hydroxy-s-triazine), mucohalogenic acids (e.g. mucochloric acid and mucophenoxychloric acid), isooxazoles, dialdehyde starch, and 1-chloro-6-hydroxytriazinylated gelatin. More specific examples of the suitable gelatin hardeners are described in U.S. Pat. Nos. 1,870,354, 2,080,019, 2,726,162, 2,870,013, 2,983,611, 2,992,109, 3,047,394, 3,057,723, 3,103,437, 3,321,313, 3,325,287, 3,362,827, 3,490,911, 3,539,644, 3,543,292, British Pat. Nos. 676,628, 825,544, 1,270,578, German Pat. Nos. 872,153, 1,090,427, 2,749,260, and Japanese Patent Publications Nos. 7133/59 and 1872/71. Of these hardeners, active vinyl compounds, active halogen compounds and aldehydes are preferred.

The gelatin hardener can be used in any amount that suits a particular object. Generally, the hardener can be used in an amount of from about 0.01 to 20% of dry gelatin. Preferably, it is used in an amount of from about 0.1 to 10 wt% of dry gelatin. If the hardener is used in an amount greater than about 20 wt% based on the weight of dry gelatin, an aqueous solution of gelatin may gel and set, making it particularly difficult to shape the aqueous solution, say, into a film by coating such as spray coating. If the content of the hardener is less than about 0.01 wt%, it is possible to make a film of the aqueous gelatin solution, but the resulting film does not harden adequately even upon drying and its strength is not satisfactory. When used in an amount in the range defined above, the hardener of this invention achieves its intended effect, i.e. quick hardening of gelatin.

The gelatin used in this invention may be "alkali treated (lime treated)" gelatin or "acid treated" gelatin, which is prepared by immersion in an alkali bath or an acid bath before extraction. Alternatively, an enzyme treated gelatin of the type described in Bull. Soc. Sci. Photo Japan, No. 16, p, 30, 1966, may be used. Gelatin of low molecular weight may also be used which is partially hydrolyzed by heating in a water bath or by treatment with a protease.

Part of the gelatin used in this invention can be optionally replaced by colloidal albumin, casein, a cellulose derivative such as carboxymethyl cellulose or hydroxymethyl cellulose, a sugar derivative such as agar, sodium alginate or a starch derivative, a synthetic hydrophilic colloid such as polyvinyl alcohol, poly-N-vinyl pyrrolidone, polyacrylic acid copolymer or polyacrylamide or derivatives or partial hydrolyzates thereof. Alternatively, the gelatin may be partially replaced with a gelatin derivative which is obtained by treating and modifying the intramolecular functional amino, imino, hydroxyl or carboxyl group with a reagent having one group that is capable of reacting with such functional groups. A portion of the gelatin may also be replaced with a graft polymer wherein gelatin is bound with the molecular chain of another polymeric substance.

Examples of the reagent for making the above gelatin derivative include isocyanates, acid chlorides or acid anhydrides as described in U.S. Pat. No. 2,614,928, acid anhydrides as described in U.S. Pat. No. 3,118,766, bromoacetic acid as described in Japanese Patent Publication No. 5514/64, phenylglycidyl ethers as described in Japanese Patent Publication No. 26845/67, vinyl sulfone compounds as described in U.S. Pat. No. 3,132,945, N-allylvinylsulfonamides as described in British Pat. No. 861,414, maleinimide compounds as described in U.S. Pat. No. 3,186,846, acrylonitriles as described in U.S. Pat. No. 2,594,293, polyalkylene oxides as described in U.S. Pat. No. 3,312,553, epoxy compounds as described in Japanese Patent Publication No. 26845/67, acid esters as described in U.S. Pat. No. 2,763,639 and alkane sultones as described in British Pat. No. 1,033,189.

This invention finds much utility as a method of hardening gelatin, and it can be used with particular advantage as a method of hardening the gelatin in a gelatin-containing layer of a silver halide photographic sensitive material. Examples of the gelatin-containing layer are a silver halide emulsion layer, a surface protective layer, an inter layer, a filter layer, an antihalation layer, a subbing layer, and a backing layer.

The silver halide emulsion used in this invention is usually prepared by mixing the solution of a water-soluble silver salt (e.g. silver nitrate) with the solution of a water-soluble halogen salt (e.g. potassium bromide) in the presence of the solution of a water-soluble polymer, e.g. gelatin. Examples of the suitable silver halide are silver chloride, silver bromide and mixed silver halides such as silver chlorobromide, iodobromide and chloroiodobromide. These photographic emulsions are described in such publications as Mees, The Theory of Photographic Process, MacMillan & Co., and P. Grafikides, Chimie Photographique, Paul Montel, 1957.

These photographic emulsions may incorporate therein various additives to prevent a drop in sensitivity or fog from occurring in the production, storage or processing of a photosensitive material. A great many compounds are known as these additives, and they include 4-hydroxy-6-methyl-1,3,3a,7-tetrazaindene, 3-methyl-benzothiazole, 1-phenyl-5-mercaptotetrazole, various heterocyclic compounds, silver hydrate compounds, mercapto compounds and metal salts. Some specific examples of the suitable compound are mentioned in K. Mees, The Theory of the Photographic Process, 3rd ed. 1966, pp. 344–349 by reference to the papers which first reported such compounds.

When the polymer of this invention is used in a photographic sensitive material, the photographic emulsion layer and other layers may incorporate therein one or more synthetic polymer compounds, such as a water-dispersed vinyl polymer of a latex type (such as polyalkyl acrylate), that increase the dimensional stability of the photographic material. These compounds may be used in combination with hydrophilic water-permeable colloids.

The polymer of this invention can be used in a photographic sensitive material together with a matting agent. A suitable matting agent is fine particles of a water-insoluble organic or inorganic compound having an average size of from about 0.2 to 10 microns, and fine particles comprising polymethyl methacrylate or silicon dioxide are particularly preferred.

The photographic sensitive material of this invention may contain a color coupler. Examples of a yellow coupler are known open-ring ketomethylenic couplers. Benzoylacetanilide and pivaloylacetanilide compounds are used with advantage. Specific examples of the applicable yellow coupler are described in U.S. Pat. Nos. 2,875,057, 3,265,506, 3,408,194, 3,551,155, 3,582,322, 3,725,072, 3,891,445, German Pat. No. 1,547,868, German Patent Application (OLS) Nos. 2,219,917, 2,261,361, 2,414,006, British Pat. No. 1,425,020, Japanese Patent Publication Nos. 10783/76, Japanese Patent Application (OPI) Nos. 26133/72, 73148/73, 102636/76, 6341/75, 123342/75, 130442/75, 21827/76, 87650/75, 82424/77 and 115219/77 (The term "OPI" as used herein refers to a "published unexamined Japanese patent application".).

Suitable magenta couplers are pyrazolone compounds, indazolone compounds and cyanoacetyl compounds, and pyrazolone compounds are used with advantage. Specific examples of the applicable magenta coupler are described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908, 3,891,445, German Pat. No. 1,810,464, German Patent Application (OLS) Nos. 2,408,665, 2,417,945, 2,418,959, 2,424,467, Japanese Patent Publication Nos. 6031/65, 45990/76, Japanese Patent Application (OPI) Nos. 20826/76, 58922/77, 129538/74, 74027/74, 159336/75, 42121/77, 74028/74, 60233/75, 26541/76 and 55122/78.

Suitable cyan couplers are phenolic compounds and naphthol compounds. Specific examples of the cyan coupler are described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411, 3,004,929, German Patent Application (OLS) Nos. 2,414,830, 2,454,329, Japanese Patent Application (OPI) Nos. 59838/73, 26034/76, 5055/73, 146828/76, 69624/77 and 90932/77.

Suitable colored couplers are exemplified in U.S. Pat. Nos. 3,476,560, 2,521,908, 3,034,892, Japanese Patent Publication Nos. 2016/69, 22335/63, 11304/67, 32461/69, Japanese Patent Application (OPI) Nos. 26034/76, 42121/77, German Patent Application (OLS) No. 2,418,959.

Suitable DIR couplers are exemplified in U.S. Pat. Nos. 3,227,554, 3,617,291, 2,701,783, 3,790,384, 3,632,345, German Patent Application (OLS) Nos. 2,414,006, 2,454,301, 2,454,329, British Pat. No. 953,454, Japanese Patent Application (OPI) Nos. 69624/77, 122335/74, and Japanese Patent Publication No. 16141/76.

Besides the DIR coupler, a compound that releases a development restrainer as development proceeds may be incorporated in the photosensitive material. Examples of such compound are described in U.S. Pat. Nos. 3,297,445, 3,379,529, German Patent Application (OLS) Nos. 2,417,914, Japanese Patent Application (OPI) Nos. 15271/77 and 9116/78.

Two or more of the couplers mentioned above may be incorporated in the same layer. Instead, the same compound may be incorporated in more than one layer. These couplers are used in an amount which generally ranges from $2 \times 10^{-3}$ to 2 mols, preferably from $1 \times 10^{-2}$ to $5 \times 10^{-1}$ mol, per mol of silver in an emulsion layer.

These couplers can be incorporated in a silver halide emulsion layer by a known method, for example, the method described in U.S. Pat. No. 2,322,027. For instance, the couplers are dispersed in a hydrophilic colloid after they are dissolved in solvents such as phthalic acid alkyl esters (e.g. dibutyl phthalate and dioctyl phthalate), phosphoric acid esters (e.g. diphenyl phosphate, triphenyl phosphate, tricresylphosphate and dioctyl butyl phosphate), citric acid esters (e.g. tributyl acetylcitrate), benzoic acid esters (e.g. octyl benzoate), alkylamides (e.g. diethyllaurylamide), aliphatic acid esters (e.g. dibutoxyethyl succinate and dioctyl azealate), or organic solvents boiling at about 30° to 150° C., for example, lower alkyl acetates such as ethyl acetate and butyl acetate, ethyl propionate, secondary butyl alcohol, methyl isobutyl ketone, $\beta$-ethoxyethyl acetate, and methyl cellosolve acetate. Mixtures of the above mentioned high-boiling and low-boiling organic solvents may be used with advantage.

A photographic emulsion for use in a photographic sensitive material to which the polymer of this invention is applied may contain one or more surfactants. Surfactants are primarily used as a coating aid, but they are sometimes used for other purposes such as for effective dispersion, sensitization, improvement of the photographic characteristics, antistatic treatment, and antiblocking treatment. These surfactants consist of natural surfactants such as saponin, nonionic surfactants such as alkylene oxide-, glycerin- and glycidol-based compounds, cationic surfactants such as higher alkylamines, quaternary ammonium salts, pyridine and other heterocyclic compounds, phosphoniums or sulfoniums, anionic surfactants containing carboxylic acid, sulfonic acid, phosphoric acid, acidic groups such as a sulfate ester group and a phosphate ester group, and amphoteric surfactants such as amino acids, aminosulfonic acids, and sulfate or phosphate ester of aminoalcohol.

When this invention is applied to a silver halide photosensitive material, further reference can be had to *Research Disclosure*, Vol. 176, pp. 22–28 (1978) for the preparation of silver halide, chemical sensitizer, antifoggant, spectral sensitizing dye, polymer latex, matting agent, brightening agent, surfactant, plasticizer, lubricant, antistatic and support.

When the polymer of this invention is used, each layer of a photographic sensitive material can be applied by various known coating methods such as dip coating, airknife coating, curtain coating, spray coating, and extrusion coating that uses a hopper as described in U.S. Pat. No. 2,681,294. If desired, two or more layers can be applied at the same time according to the method described, for example, in U.S. Pat. Nos. 2,761,791, 3,508,947, 2,941,898 and 3,526,528.

There is no particular limitation on the method of exposing and developing a photographic sensitive material that contains the polymer of this invention, and if necessary, reference can be made to *Research Disclosure*, Vol. 176, pp. 28–30 (1978).

The monomers used to prepare the benzenesulfinic acid containing polymers used in this invention can be synthesized by the following illustrative methods, but the invention is by no means limited to these examples.

I. Synthesis of sodium salt of vinyl benzenesulfinic acid (Compound A)

I-1. Synthesis of p-(β-bromoethylbenzene)sulfonyl chloride

A measured amount (84.3 g) of 30% fuming sulfuric acid was placed in a three-necked flask with a stirrer, and at a controlled temperature of 20° to 23° C., a mixture of 58.8 g (0.32 mol) of commercial β-bromoethylbenzene and 26.1 g of acetonitrile (0.636 mol) was added to the flask dropwise. Thereafter, the temperature of the reaction mixture was elevated to 40° to 45° C. at which 92.3 g (0.795 mol) of chlorosulfonic acid was added dropwise. Following the dropwise addition, the reaction mixture was held at 40° to 45° C. for a while until the reaction was terminated. The reaction mixture was poured into one liter of ice water, and the resulting crystal was filtered off, dried, and recrystallized from hexane. The end compound having a melting point of 54° to 55° C. was obtained in a yield of 59%.

I-2. Synthesis of p-(β-bromoethylbenzene)sulfinic acid

A measured amount (42.5 g) (0.15 mol) of the p-(β-bromoethylbenzene)sulfonyl chloride and 210 cc of glacial acetic acid were placed in a 500-cc three-necked flask, and under stirring, 12.8 g of zinc powder was added to the flask at 25° to 35° C. Thereafter, the mixture was stirred for an hour at 35° C., and after the addition of 128 ml of concentrated hydrochloric acid and 106 ml of water, the temperature of the reaction mixture was elevated to about 80° C. When the content was dissolved completely, the reaction mixture was cooled with ice, and the resulting crystal was filtered off and recrystallized from water. The end compound having a melting point of 105° to 107° C. was obtained in a yield of 42%.

I-3. Synthesis of sodium salt of vinylbenzenesulfinic acid (Compound A)

A mixture of 12.7 g (0.051 mol) of the 2-bromoethylbenzenesulfinic acid, 10.0 g (0.153 mol) of caustic potash, 237 ml of methanol and 0.14 g of hydroquinone was placed in a 500-cc three-necked flask and heated under reflux for an hour. Thereafter, the methanol was dried to form a solid which was mixed with 80 ml of water and 9 ml of concentrated hydrochloric acid. The resulting mixture was cooled with ice, and the crystal of vinylbenzenesulfinic acid was filtered off, dissolved in water, neutralized with caustic soda, and the water was distilled off to yield 60% of end product having a melting point of at least 200° C.

II. Synthesis of sodium p-(α-methylvinyl)benzenesulfinate (Compound C)

α-methylstyrene was treated with chlorosulfonic acid in the manner of Synthesis I-1 to prepare p(-α-methylvinyl)benzenesulfonyl chloride. The chloride was reduced in the manner of Synthesis I-2, and neutralized with caustic soda to yield 36% of sodium p-(α-methylvinyl)benzenesulfinate having a melting point of at least 200° C.

III. Synthesis of sodium vinylbenzene-2,4-disulfinate (Compound E)

According to Tr. Vses Nauch-Issed. Inst. Khim. Reactiv. Osobo. Chist. Khim. Veschestv, No. 33, p. 22–29, (1971), a barium salt of 1-(2-bromoethyl)benzene-2,4-disulfonic acid was reacted in a conventional manner with chlorosulfonic acid to form 1-(2-bromoethyl)benzene-2,4-disulfonic acid chloride. The chloride was reduced in the manner of Synthesis I-2 to give 1-(2-bromoethyl)benzene-2,4-disulfinic acid which was vinylated in the manner of Synthesis I-3 to form vinylbenzene-2,4-disulfonic acid.

A homopolymer of vinyl benzene sulfinate salt included in the formula (I) can be synthesized according to Chem. Lett., pp. 419–420, 1976. The polymer can also be prepared by any conventional polymerization method. Copolymers of vinylbenzenesulfinate salt can be synthesized by any known polymerization method, e.g. the method described in W. R. Sorenson & T. W. Campbell, *Experimenting Synthesis Polymers* (Tokyo Kagaku Dojin), pp. 147 and 157. The polymer can achieve the intended objects of this invention whether it is used as a solution in water or organic solvent or dispersion in water.

As already mentioned, the polymer having a repeating unit of the formula (I) can be prepared by polymerizing a monomer of the formula (II) or by introducing a sulfinic group into a separately prepared polymer. For example, a chlorosulfonated polystyrene can be prepared from polystyrene or poly(α-methylstyrene) in the manner of Synthesis I-1, and a polystyrene having a sulfinic group in the benzene nucleus can be produced in the manner of Synthesis I-2.

Synthesis Example 1

Synthesis of Compound (1)

A mixture of 30.0 g of sodium salt of vinylbenzenesulfinic acid and 1.5 g of potassium persulfate was dissolved in 300 cc of distilled water and the mixture in aqueous solution was polymerized in a nitrogen stream at 70° C. for 24 hours. Thereafter, the aqueous solution was dialyzed with distilled water for 24 hours and freeze-dried. The yield of the polymer was 22.6 g. It had an intrinsic viscosity ($\eta_{sp}/c = 0.2$ wt%) of 1.388 in a 1.5 mol aqueous solution of sodium bromide.

Synthesis Example 2

Synthesis of Compound (4)

A mixture of 10.0 g of sodium salt of vinylbenzenesulfinic acid, 5.83 g of N-vinylpyrrolidone and 0.570 g of the hydrochloride of 2,2'-azobis(2-amidinopropane) was dissolved in 200 cc of distilled water and subjected to polymerization in the same manner as in Synthesis Example 1. The end compound was obtained in a yield of 16.0 g.

Synthesis Example 3

Synthesis of Compound (7)

A mixture of 15.0 g of sodium salt of vinylbenzenesulfinic acid, 5.8 g of potassium salt of vinylbenzenesulfonic acid and the hydrochloride of 2,2'-azobis(2-amidinopropane) was dissolved in 200 cc of distilled water, and polymerization was performed in the same manner as in Synthesis Example 1. The yield of the polymer was 19.9 g. It had an intrinsic viscosity ($\eta_{sp}/c = 0.2$ wt%) of 1.850 in a 1.5 mol aqueous solution of sodium bromide.

Synthesis Example 4

Synthesis of Compound (11)

A mixture of 10 g of sodium salt of vinylbenzenesulfinic acid, 1.13 g of vinyl acetate, and 0.356 g of 2,2'-azobisisobutyronitrile was dissolved in 200 cc of methanol and polymerized at 60° C. for 24 hours. The aqueous solution was then dialyzed with distilled water for 24 hours and freeze-dried.

Synthesis Example 5

Synthesis of Compound (12)

Compound (11) was dissolved in dilute caustic soda, thoroughly hydrolyzed at 60° C., dialyzed and freeze-dried.

The method of this invention can be used with advantage in processing not only photographic sensitive materials but also any photographic materials that require hardening of gelatin, such as microcapsules for pressure-sensitive copying paper. Microcapsules can be produced by, for example, by the complex coacervation described in U.S. Pat. No. 4,016,098. Microcapsules are hardened as follows: the gelatin wall membrane formed by coacervation is cooled to gel and is hardened in the presence of a gelatin hardener, optionally together with an alkali (e.g. NaOH) to provide an alkaline reaction condition. Alternatively, the gelatin hardener is added after the pH of the reaction system is adjusted to alkaline. According to the method of this invention, the polymer having a repeating unit of the formula (I) as well as a gelatin hardener are incorporated in the microcapsule to make it harden at a faster rate. For hardening a microcapsule, the polymer of this invention and gelatin are used in the same proportion as defined for a photographic sensitive material.

This invention is hereunder described in greater detail by reference to the following examples that illustrate the application of the invention to silver halide photographic sensitive material, but it should be understood that the scope of this invention is by no means limited to such examples.

EXAMPLE 1

A high-sensitivity negative emulsion was prepared by performing optimum ripening of a silver iodobromide emulsion containing 6.0 mol% of silver iodide using a sulfur sensitizer and a gold sensitizer well known to those skilled in the art. To this emulsion, a spectral sensitizer (anhydro-5,5'-tetrachloro-1,1'-diethyl-3,3'-di(3-sulfopropyl)benzimidazolocarbocyanine hydroxide), a stabilizer (4-hydroxy-6-methyl-1,3,3a,7-tetrazaindene) and a magenta coupler comprising an emulsion of 1-(2',4',6'-trichlorophenyl)-3-[3''-(2''',4'''-di-tert-aminophenoxyacetamido)benzamido]-5-pyrazolone were added to prepare a color negative photographic emulsion for use in a green-sensitive layer. The magenta coupler was added to the high-purity negative emulsion by first dissolving tricresyl phosphate in ethyl acetate and dispersing the coupler in gelatin with the aid of sodium dodecylbenzenesulfonate. An emulsion protective layer was prepared by adding 1.5 g of 1,3-bis(vinylsulfonyl)propane per 100 g of gelatin. Such protective layer plus the color negative photographic emulsion for use in a green-sensitive layer was divided into four equal portions. One of them was set aside as a control. The other three portions were mixed with 4 g of the compounds (1), (4) and (7), respectively, of this invention per 100 g of gelatin. Coating solutions containing these four portions were applied to a cellulose triacetate support having a suitable subbing layer to provide coatings such containing $1.5 \times 10^{-3}$ mol/m² of the coupler.

Drying gave samples (1), (2), (3) and (4). Each sample was exposed to green radiation using an SNG type II sensitometer and subjected to color development as described in Example 1 of Japanese Patent Application (OPI) No. 51940/76. The samples were then allowed to stand at 25° C. and 65% RH for 15 days, and the measurement of their relative sensitivity and fog density was made on the 3rd, 5th and 15th days. The results of the measurement are set forth in Table 1 below. Part of each sample was cut away on the 1st, 3rd, 5th and 15th days, and it was measured for the swell (Q) in water at 25° C. that is given by the following formula:

$$Q = \frac{\text{Increase in film thickness upon swelling}}{\text{thickness of dry film}} \times 100$$

The results of the measurement are also indicated in Table 1.

TABLE 1

| | Swell (Q) | | | |
|---|---|---|---|---|
| | Days Past | | | |
| Sample No. | 1 | 3 | 5 | 15 |
| (1) Control | 6.8 | 4.8 | 4.0 | 3.2 |
| (2) Compound (1) | 5.1 | 4.0 | 3.6 | 3.4 |
| (3) Compound (4) | 5.4 | 3.9 | 3.5 | 3.4 |
| (4) Compound (7) | 4.7 | 3.7 | 3.4 | 3.2 |

| | Relative sensitivity* and fog density | | |
|---|---|---|---|
| | Days Past | | |
| Sample No. | 3 | 5 | 15 |
| (1) | 100 (0.15) | 95 (0.15) | 92 (0.15) |
| (2) | 92 (0.15) | 91 (0.15) | 91 (0.15) |
| (3) | 98 (0.17) | 97 (0.17) | 96 (0.17) |
| (4) | 92 (0.15) | 91 (0.15) | 91 (0.15) |

FOG density is parenthesized.

*The relative sensitivity is based on the sensitivity (100) of sample (1) measured on the 3rd day which is the reciprocal of an exposure on log. scale that provides a fog density +0.10.

Table 1 clearly shows that compounds (1), (4) and (7) had the effect of increasing the hardening speed of gelatin. This is reflected in the fact that the swell, sensitivity and fog density of samples (2), (3) and (4) containing these compounds settled down at certain values faster than the control without imparing their photographic characteristics.

EXAMPLE 2

An emulsion protective layer plus a color negative emulsion for use in a green-sensitive layer prepared in the same manner as in Example 1 was divided into four equal portions. One of them was set aside as a control, and the other three portions were mixed with 4 g of the compounds (1), (3) and (8), respectively, of this invention per 100 g of gelatin. Coating solutions containing the four portions were applied to a polyethylene terephthalate support (having a suitable subbing layer) to provide coatings 5 microns thick. Drying gave samples (11), (12), (13) and (14). Each sample was stored for two or twenty days at 25° C. and 65% RH. It was also subjected to heat treatment for two days at 50° C. and 80% RH. The strength of the membrane of each sample was measured by the following two methods.

1. Strength of membrane surface: The sample was immersed in water (25° C.) for 5 minutes. A needle having a steel ball (0.4 mm in radius) attached thereto was pressed against the sample and was moved parallel on the surface of the membrane at 5 mm/sec., with the load applied to the needle varying continuously in the range of from 0 to 200 g. The load (in grams) that impaired the surface of the sample physically was measured.

2. Time to dissolve: Small pieces of each sample were immersed in 0.5 N caustic soda at 60° C. until the emulsion membrane began to dissolve. The time required for such dissolution was measured.

The results of the measurement are set forth in Table 2 below.

TABLE 2

| Sample No. | Strength of membrane surface (g) Days Past | | | | Time to dissolve (sec.) Days Past | | | |
|---|---|---|---|---|---|---|---|---|
| | 2 | 20 | 2 | (50° C. 80% RH) | 2 | 20 | 2 | (50° C. 80% RH) |
| (11) Control | 60 | 115 | 139 | | 350 | 670 | 680 | |
| (12) Compound (1) | 80 | 130 | 158 | | 505 | 770 | 775 | |
| (13) Compound (3) | 78 | 132 | 144 | | 500 | 685 | 690 | |
| (14) Compound (8) | 70 | 110 | 140 | | 485 | 680 | 685 | |

Table 2 shows that the polymers of this invention did not provide a membrane low in the strength of its surface or a membrane which dissolves in concentrated caustic soda in a short period.

EXAMPLE 3

A high-sensitivity negative photographic emulsion containing 120 g of gelatin and 65 g of silver iodobromide per kilogram was prepared in a conventional manner, and to this emulsion, 1.5 g of 1,3-bis(vinylsulfonyl)-2-hydroxypropane was added per 100 g of gelatin. The resulting emulsion was divided into four equal portions. One of them was set aside as a control, and the remaining three portions were mixed with 4 g of compounds (1), (4) and (7), respectively, of this invention per 100 g of gelatin. Coating solutions containing the four portions were applied to a cellulose triacetate support (having a subbing layer) to provide uniform coatings in a dry thickness of 5 microns. Drying gave samples (21), (22), (23) and (24). Each sample was left to stand at room temperature for 15 days, and the swell in water at 25° C. was measured on the 1st, 3rd, 7th and 15th days. The samples were also subjected to wedge exposure, developed with a D-76 developer at 20° C. for 8 minutes, fixed, washed with water, dried and measured for their sensitivity and fog density by sensitometry. The results of the measurement are set forth in Table 3 below.

TABLE 3

| Sample No. | Swell Days Past | | | | Relative sensitivity & (fog density) Days Past | |
|---|---|---|---|---|---|---|
| | 1 | 3 | 7 | 15 | 2 | 50° C. 2* |
| (21) Control | 6.7 | 5.1 | 4.0 | 3.2 | 100 (0.08) | 92 (0.09) |
| (22) Compound (1) | 5.2 | 4.0 | 3.6 | 3.4 | 91 (0.08) | 90 (0.09) |
| (23) Compound (4) | 5.4 | 4.1 | 3.6 | 3.5 | 98 (0.10) | 97 (0.11) |
| (24) Compound (7) | 4.9 | 3.9 | 3.6 | 3.5 | 94 (0.08) | 93 (0.09) |

*(under accelerated hardening)

The samples (22), (23) and (24) prepared by this invention had good "after-hardening characteristics" in that their swell settled down at certain levels faster than the sample (21) which was hardened in the presence of a hardener alone.

Table 3 clearly shows that the samples prepared by this invention exhibited well balanced photographic characteristics in that they experienced less change in the relative sensitivity and fog density than the control at various levels of temperature and humidity.

While the invention has been described in detail and with reference to specific embodiments thereof, it will be apparent to one skilled in the art that various changes and modifications can be made therein without departing from the spirit and scope thereof.

What is claimed is:

1. A method of hardening gelatin in which said gelatin is hardened by both a gelatin hardener and a polymer having at least 0.01 mol % of a repeating unit of the formula (I):

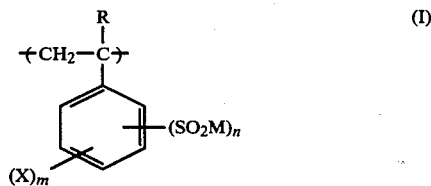

wherein R represents a hydrogen atom, an alkyl group having 1 to 6 carbon atoms, and a halogen atom; M represents a hydrogen atom, an alkali metal atom, an alkali earth metal atom, or an organic base; X represents an alkyl group having 1 to 6 carbon atoms, an alkoxy group, an alkylamino group, or a halogen atom; m represents 0, 1 or 2; and n represents 1 or 2.

2. The method of claim 1 wherein said polymer is a homopolymer or copolymer.

3. The method of claim 1 wherein said polymer has a number average molecular weight of about 1,000 to 2,000,000.

4. The method of claim 1 wherein said gelatin hardener is selected from the group consisting of aldehydes, N-methylol compounds, dioxane derivatives, active vinyl compounds, active halogen compounds, mucohalogenic acid isooxazoles, dialdehyde starch, and 1-chloro-6-hydroxytriazinylated gelatin.

5. The method of claim 1 wherein said gelatin hardener is present in an amount of about 0.01 to 20 wt% based on the amount of dry gelatin.

6. The method of claim 1 wherein said polymer is present in an amount of about 0.01 to 99 wt% based on the total amount of gelatin and polymer.

7. The method of claim 1 wherein M represents a hydrogen atom, a sodium atom, a potassium atom, a calcium atom, or a magnesium atom.

8. In a photographic material containing a gelatin emulsion layer, the improvement wherein said gelatin is hardened with a gelatin hardener and a polymer having at least 0.01 mol % of a repeating unit of the formula (I):

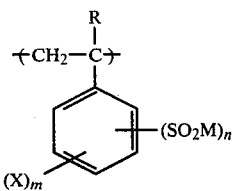

wherein R represents a hydrogen atom, an alkyl group having 1 to 6 carbon atoms, and a halogen atom; M represents a hydrogen atom, an alkali metal atom, an alkali earth metal atom, or an organic base; X represents an alkyl group having 1 to 6 carbon atoms, an alkoxy group, an alkylamino group, or a halogen atom; m represents 0, 1 or 2; and n represents 1 or 2.

9. In a method for forming microcapsules by co-acervating gelatin and hardening the gelatin wall, the improvement which comprises hardening said gelatin wall using both a gelatin hardener and a polymer having at least 0.01 mol % of a repeating unit of formula (I):

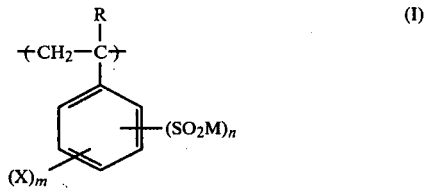

wherein R represents a hydrogen atom, an alkyl group having 1 to 6 carbon atoms, and a halogen atom; M represents a hydrogen atom, an alkali metal atom, an alkali earth metal atom, or an organic base; X represents an alkyl group having 1 to 6 carbon atoms, an alkoxy group, an alkylamino group, or a halogen atom; m represents 0, 1 or 2; and n represents 1 or 2.

* * * * *